United States Patent [19]

Farrar et al.

[11] 4,281,659
[45] Aug. 4, 1981

[54] APPLYING AND SECURING PERCUTANEOUS OR TRANSCUTANEOUS PROBES TO THE SKIN ESPECIALLY FOR FETAL MONITORING

[75] Inventors: Alfred O. Farrar, Cranbury; Howard M. Hochberg, East Windsor, both of N.J.

[73] Assignee: Roche Medical Electronics Inc., Cranbury, N.J.

[21] Appl. No.: 19,550

[22] Filed: Mar. 12, 1979

[51] Int. Cl.$^3$ .......................... A61B 5/00; A61B 5/04
[52] U.S. Cl. .................................. 128/635; 128/640; 128/642; 204/195 B
[58] Field of Search ................. 128/632, 635, 639–644, 128/783–786, 788, 798, 802, 803; 204/195 B, 195 P

[56] References Cited

U.S. PATENT DOCUMENTS

| | | | |
|---|---|---|---|
| 3,659,586 | 5/1972 | Johns et al. | 128/635 |
| 3,848,582 | 11/1974 | Milani et al. | 128/639 |
| 3,973,555 | 8/1976 | Moller et al. | 128/635 |
| 4,066,085 | 1/1978 | Hess | 128/785 |
| 4,067,321 | 1/1978 | Oda et al. | 128/640 |
| 4,094,305 | 6/1978 | Kessler | 128/635 |

FOREIGN PATENT DOCUMENTS

| | | | |
|---|---|---|---|
| 1907378 | 9/1969 | Fed. Rep. of Germany | 128/639 |
| 2061593 | 6/1972 | Fed. Rep. of Germany | 128/642 |
| 2724461 | 12/1977 | Fed. Rep. of Germany | 128/635 |

OTHER PUBLICATIONS

Huch et al., "Transcutaneous Measurement of $PO_2$...", J. Perinat. Med., 1 (1973), 183.
Scacci et al., "$O_2$ Tension Monitoring", Med. Inst., vol. 10, No. 4, pp. 192–194, Jul.–Aug. 1976.
Vesterager, "Continuous Trans. ... $PO_2$", *Measurement of $O_2$*, 1976, pp. 260–270.

*Primary Examiner*—Lee S. Cohen
*Attorney, Agent, or Firm*—Jon S. Saxe; Bernard S. Leon; George M. Gould

[57] ABSTRACT

Apparatus and method for securely and stably fastening a probe such as a pH electrode to a patient such as a fetus undergoing labor, and a locking applicator tool arrangement for effecting the attachment of such apparatus. The fastening device is a generally cylindrical piece having a broad concave operative surface with a helical wire screw centrally protruding therefrom and a trio of small pods equispaced on the periphery thereof. An axial threaded hole extends from the concave surface through the rear portion of the device for accepting the probe. The rear portion of the device is configured to cooperate with the locking applicator tool arrangement which comprises an inner tubular member for holding the device in its one end and a concentrically arranged outer locking tubular member for controlling the locking and release of the device. The applicator assembly further comprises a stab tool configured to be applied to the patient through the holding tubular member and the fastening device and also an applicator member for effecting attachment of the probe to the fastening device through the holding tubular member.

16 Claims, 31 Drawing Figures

APPLYING AND SECURING PERCUTANEOUS OR TRANSCUTANEOUS PROBES TO THE SKIN ESPECIALLY FOR FETAL MONITORING

BACKGROUND OF THE INVENTION

The present invention relates to applying and securing percutaneous or transcutaneous probes, such as pH electrodes, to the skin, especially especially in connection with fetal monitoring.

A variety of percutaneous and transcutaneous probes are used for measuring and monitoring patients. For safety, if nothing else, they must be firmly fastened or they might migrate and cause damage (e.g. migration of an arterial catheter through the arterial wall). In addition, some probes must be firmly fixed or their motion will tend to pull the fastening means (e.g. tape) off. Moreover, the motion may affect the accuracy of the reading due to the motion itself, displacement from a desired location or tissue damage caused by the moving probe.

In particular, there is a need for firm, safe attachment of relatively large, bulky or heavy transcutaneous biochemical probes, such as are employed for measuring pH, and especially to difficult locations, such as the fetal scalp.

PH as a measure of the "activity" of the hydrogen ion in solutions, and a prime influence on the rate of many bio-chemical reactions, including the pharmacologic properties of drugs, is a parameter of especial importance in determining quickly the state of well-being of an organism.

Fetal pH monitoring in particular has recently enjoyed a considerable upsurge in interest. Capillary pH from blood obtained from the presenting part is a well known measure of the metabolic and respiratory status of the fetus. It is particularly useful when fetal hypoxia is suspected from the fetal heart rate patterns, or from other clinical criteria.

The continuous measurement and display of interstitial tissue fluid pH (tpH) in particular is enjoying recent interest and increased importance from clinicians, researchers and physicians in general. The present clinical practice of intrapartum fetal monitoring routinely includes intermittent sampling of fetal capillary blood pH, which is believed by a growing body of experts to be closely approximated by tpH. TpH has recently been found to be more labile than heretofore appreciated, and single capillary samples may be unrepresentative of the trend of events.

Tissue pH has been studied in animals as well as human adult and pediatric patients. Until recently, these efforts required insertion of two probes several centimeters long between muscles fibres. Although data derived therefrom is considered valuable, and does reflect tissue status, this method is not generally accepted or practical.

Several investigators have also tried to assess fetal scalp capillary blood or tissue pH with standard pH electrodes, but have found it impossible to surmount the technical problems of maintaining the electrodes in place, of preventing drift and inaccuracy due e.g. to "poisoning" of the electrode and other known and unknown factors, and of maintaining readings in the face of changes of tissue pressures, as occur during contractions.

It has been noted that the subcutaneous tissue fluid pH closely approximates capillary pH; and from this encouraging development a single pH probe was designed to be placed through the skin into the subcutaneous tissue (developed by Stamm and Moeller). The continuous measurement of subcutaneous interstitial fluid or tissue pH was thus made practical by this development of a miniaturized short, self-contained guarded glass pH electrode and reference electrode arrangement. This electrode, together with appropriate safety matched, accurate electronics (which provide error checking, autocalibration, etc.), provides a complete tissue pH monitor and display system.

In spite of these developments, the tpH electrode must be properly inserted and maintained in position in order to ensure accuracy of reading and data derived therefrom. A satisfactory arrangement for application of such probes, especially for fetal monitoring, which ensures proper insertion and electrode positional stability following application, has hitherto been unavailable.

With particular regard to intrapartum fetal monitoring, it is considered necessary for the tpH electrode to be affixed substantially perpendicular to the fetal skin surface, while placing the tip of the active probe only about four millimeters below the skin surface.

New means are therefore required for the proper insertion of such probes while maintaining a stability of placement thereof for relatively long periods of time for continuous monitoring. In addition, such means must be able to reduce torque, shear, tension and bending stresses on or from the probe, and must be able to distribute the load in such a manner as to minimize stress concentrations, and thereby minimizing the chances for tissue damage and artifactual readings. Present devices for attaching probes, such as adhesive tapes or double spiral screws to be screwed into the skin, are inapplicable to most locations and/or do not afford adequate protection against such bending, torque, etc., stresses and forces. In short, they permit too much probe motion and too little stability. In particular regard to the present screw type electrode arrangements, these rely on the screws for retention, but substantially all forces are transmitted through the screws to the tissues, thus producing unacceptable high stress concentrations.

It is, therefore, a principal object of this invention to provide simple yet effective fixation of percutaneous or transcutaneous probes, and provide in connection therewith the afore-mentioned desirable features and yet overcome the drawbacks of the prior art. In particular, it is a part of said object to provide force distribution to reduce stress concentrations and thereby minimize tissue damage and artifactual readings, especially in the usually relatively difficult situation of the intra partum monitoring of the fetus.

In securing such probes to, into or in particular through the skin, it is deemed far safer to hold the skin retracted from the underlying tissues (and/or bone) to produce a real subcutaneous tissue space for the probe from the virtual space, and, in addition, to hold the probe away from the underlying tissues per se. The immediate advantage of this is to prevent possible false readings due to the underlying tissue or due to pressure on the electrode, to prevent damage to the underlying tissue by the electrode, and to prevent damage to the electrode from underlying tissues.

It is therefore another principal objective of this invention to provide a securing arrangement for such probes that provides the above-mentioned additional advantageous features.

It is an additional objective of this invention to provide such arrangements in a form which is entirely compatible with other monitoring functions such as fetal ECG, $pO_2$ etc.

It is a further objective to provide a pH electrode applicator/retaining arrangement wherein the electrode tip is held away from the underlying tissues and the skin is also held retracted therefrom during insertion of the probe and thereafter, as desired.

It is yet another object to provide an electrode applicator/retaining arrangement in which during and following insertion of the probe, the depth thereof in and beneath the skin can be continuously controlled by the retaining arrangement per se and the pressure against the probe continuously accommodated, even in the face of for example the skin becoming thinner.

It is yet a further object to provide fault indication if the probe is not properly seated in the subcutaneous region.

It is still another object to provide an applicator arrangement for safe and easy attachment of a spiral type electrode holder, the guiding of a stab blade into centered position through the holder to make a small incision in the skin of the patient's presenting part as is needed e.g. for a pH probe, and for the insertion of the probe properly centered and stabilized in the incision.

SUMMARY OF THE INVENTION

In accordance with the broader aspects of the invention there is provided an apparatus for securing biomedical monitoring means such as a probe to or through the skin of an organism, comprising:
a base having a body portion and an operative face;
first means associated to said body portion for firmly yet detachably securing the monitoring means to the base,
second means associated to said operative face of the base for securing the base to the skin of the organism and thereby the monitoring means to the organism.
said operative face and body portion of the base being configured to effectively stabilize the position of the monitoring means relative to the organism in the presence of forces tending to move or reorient the secured base relative to the surface of the organism's skin, through the distribution of such forces to and over a skin surface area at least as large as the area of the operative face of the base.

The present invention is described herein primarily in connection with embodiments which can be utilized to securely affix a transcutaneous pH (tpH) probe to the fetal presenting part (scalp) during labor. The device is comprised of a cylindrical dielectric base having a relatively large circular cup-shaped (concave) operative face from which a pair of helically arranged wires extend forming a low-pitch screw arrangement to affix the device to the skin of the fetus. Behind the operative face, the body of the device extends longitudinally in a triangular type cross-sectional configuration. The base or body has an axially located hole or bore running therethrough. Three small pods or feet are situated on the periphery of the circular cup-shaped face equally distant apart from one another which serve to further stabilize the device when in place. In the depicted example embodiments, the operative face of the device is shaped to closely approximate the curvature of the fetal skull.

The stresses of bending and shear to which the device is subjected, especially if a relatively heavy or bulky pH probe is associated therewith, are spread through the triangular cross-section buttresses to the operative surface of the base and along to a large skin surface and volume. Moreover, these forces are transmitted to the three feet, which are particularly useful if the skin is irregularly depressed at the measuring site. The relatively large area of intact tissue provides a larger base for resisting bending with less stress concentration than prior art devices. The feet and the friction of the large surface contact area spread the torque forces and help prevent torque, thus preventing an unscrewing of the electrode or excessive screwing thereof into the skin. As torque is typically the most detrimental effect of tension on the cable connecting to the rear portion of the device, this then tends to reduce the effects of tension as well.

Because of the curvature of the operative face of the device, there is a tendency to produce with the sealing effects of the fluid present during labor, a suction effect on the fetal skull, and good sealing of the measuring site from air and debris, which is particularly useful in the case of measurement of pH which requires a preliminary small stab wound.

With this device, the problems of placement and tissue pressures associated to the tpH electrode are minimized. The tpH probe itself is a single short miniaturized configuration for substantially perpendicular penetration of a few millimeters below the skin surface, and which is securable in the special wide-flanged, cup-shaped spiral-holding device of the present invention, thus providing a highly stable mode of operation. It is to be noted that especially for fetal monitoring, such an electrode arrangement should be less traumatic than standard methods with repeated sampling, because only one incision is required, there is no need to force the tissue to bleed, and especially the skin can be held away way from the bone when the incision is made.

The cup-shaped device further ensures against false readings and damage to the electrode and flesh or underlying tissues, and especially controls the depth of the probe, by having the cup-shaped device, which is attached to the skin by threading of the associated wire spirals into the skin, include a central piece or hub to which the spirals are attached, which hub is in turn threaded into the body of the cup-shaped device with a thread of the same directional sense as the spiral wire or electrode arrangement. By turning the cup-shaped device into the skin with a suitable applicator or clamp (or perhaps by hand in non-fetal cases) and restraining the hub from turning, preferably by the same applicator set, the spiral is fastened. By releasing the hub and continuing to turn in the same direction, the threaded hub would draw the spiral and the skin into the cup's recessed area. The hub itself would have the central bore for passage of the pH probe. The pH probe could be secured to the hub by a cooperative threading arrangement.

In furtherance of that most desirable feature of ensuring continuous control of the depth of the probe, and ensuring further that changes in the pressure against the electrode are accommodated, especially if the skin becomes thinner and the electrode should be too deep, means are provided for effecting automatic "back-off" of penetration in the face of such changed conditions or if the probe is somehow caused to become too deeply inserted.

This may be accomplished by having as part of the cup-shaped electrode holder a movable rigid inner piece containing threads for securing the probe or electrode. An elastic means may be permanently fastened to the inner surface of the outer rigid portion of the cup-shaped piece, and also to the top (rear) portion of the inner movable rigid piece. In this way, excessive force applied to the inner member (which holds the pH probe) by the pH probe would push against the elastic piece and force the probe out. Penetration is inversely proportional to the amount of resistance encountered and the force would be proportional to displacement. Small displacement would therefore be readily accommodated, but the inner rigid piece would not be forced far enough for the probe to be out of the skin.

The arrangement is particularly advantageous also because if one of the spirals dislodges for any reason, and thereby prevents good contact between the cup-shaped flange and the skin, as required for proper stability, the elasticity of this means would enable the pH probe to move forward to remain inserted even in the face of the partial spiral separation.

It is especially important too that the broad, cup-shaped structure facilitates the spirals drawing the tissue up to the cup center portion and thus away from the scalp, thereby providing a safer base area for application of the pH electrode.

The spirals of the present invention are of a unique configuration which allows economical manufacture thereof in an electrode structure that is intended to have a clear longitudinal passage way or bore through the center thereof.

From the inventive arrangement one is able to provide fault detection, i.e. detection of improper placement of the probe or electrode which would arise if the same is not properly seated in the subcutaneous tissue (under the skin, immune from air or external body fluids such as amniotic fluid). This may be accomplished, for example, by utilizing the spiral holding wires also as active ECG electrodes and taking readings of the resistance between the skin surface and the salt bridge of the pH probe, or of the ECG between the salt bridge and the usual ECG reference electrode, which can also be provided on the cup-shaped device, and/or of the lack of ECG and resistance between the pH reference electrode and the spiral probes.

It is to be noted further in the case of fetal monitoring that the wideness of the opertive surface of the cup-shaped flange relative to the spirals themselves, enables safe entry into and along the vagina without worrying about snagging the vagina wall during transit.

The invention is further characterized by a special applicator arrangement which permits attachment of the cup-shaped spiral-held electrode (electrode) base, effectuation of a stab wound centrally located for the pH electrode, and accurate substantially perpendicular placement of the pH electrode centrally located and in the stab wound, while promoting the necessary stability throughout application and thereafter for ensuring accurate measurements.

In an especially preferred embodiment of the applicator tool, there is included means for providing a positive manipulation for opening (i.e. release) via a cam action, instead of relying for example upon the memory of the plastic material (which, of course, varies with material dimensions, composition, age etc). Disengagement of the cup-shaped spiral holder/base from the applicator is further ensured, for example, by a locking ear/detent design which facilitates release also by a camming type surface and action.

BRIEF DESCRIPTION OF THE DRAWINGS

The above-mentioned and other objects and features and the invention itself will be better understood by reference to the following detailed description taken in conjunction with the accompanying drawings, in which.

DESCRIPTION OF THE PREFERRED EMBODIMENTS

The known devices in practical use for attaching percutaneous or transcutaneous probes to the skin essentially consist of either adhesive tapes or double spiral screws (which are screwed into the skin). Present demands, however, are requiring that the device be able to successfully resist torque, shear, tension and bending stresses from or associated to the probe, and be able to distribute the load in such a manner as to minimize stress concentrations, thus minimizing the chances for tissue damage. These loads are illustrated in connection with a typical prior art configuration depicted in FIG. 1.

The prior art tape arrangements for fastening probes to the skin are inapplicable to most locations and do not afford protection against bending or torque stresses especially. Moreover, they allow far too much probe motion. The spiral screw devices rely on the screws for retention, but substantially all the forces are transmitted through the screws to the tissues, producing high stress concentrations.

Bending and shear forces are due for example to the movement or the weight of the cable and the (pH) probe. Tugging forces on the cable produce tension as well. Torque may be produced by rotation of the subject (the fetus) or the cable, or also by tension on the cable, which tends to turn the screw fastening arrangement.

A device which solves the problem of successfully combating the various aforementioned loads and particularly with regard to affixing a transcutaneous pH (tpH) probe to the fetal scalp during labor, is illustrated in FIGS. 2A–2B and 3A–3B. In the depicted form, there is provided cylindrically shaped base 1 having a front portion 1a of a first diameter and rear portion 1b of a smaller diameter. The rearward side of front portion 1a provides a tapering surface 2 communicating with the coaxial front and rear portions 1a and 1b. The base may be composed of a rigid plastic of similar suitable material.

Figure 2A:
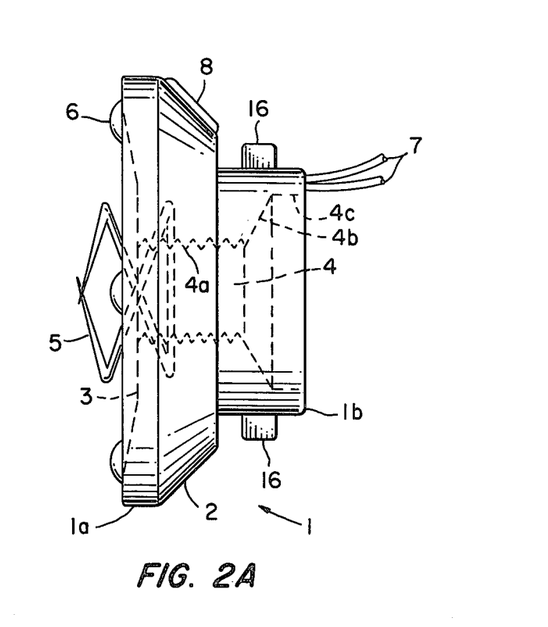
FIGS. 2A and 2B are respectively side and front views of a device for securing a probe to for example the fetal scalp, in accordance with the invention.
Figure 2B:
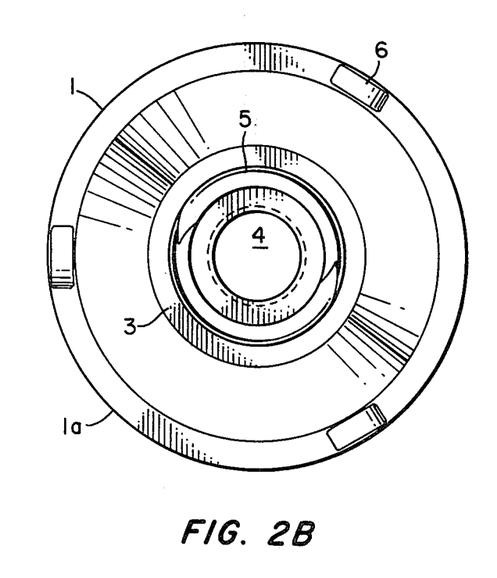

Front portion 1a has a relatively large operative face 3 which is concave in configuration to provide a "cup-shaped" surface that cooperates with the curvature of the fetal skull. A substantial part of the central area of the operative face is, however, flat. An axially located hole or bore 4 extends through the device. Bore 4 has a first diameter section 4a in the front portion 1a of the base and a larger diameter section 4b within the rear portion 1b. These two sections of the axial bore 4 are connected by a midsection 4c which is also located within the rear portion 1b of the base, which midsection 4c tapers to communicate with the diameters of the front and rear sections 4a and 4b.

Protruding from the operative face 3 are a pair of helically configured pointed wire ends 5 which break the surface 3 equidistant from and on opposite sides of the bore opening at a low angle pitch. In actuality, these spirals 5 constitute the ends of a single wire piece that is partially embedded in the plastic base 1 in the front (1a) and mid(2) portions thereof. The spiral of helix is configured (wound) in such a way that a single piece of wire can be used without interfering with the axial bore 4 or the space in front of the bore section 4a. For a more detailed appreciation of the spiral wire's configuration see the enlarged view of FIG. 14.

Located near the rim of the operative face 3 are a trio of equispaced apart pods 6, each extending in length circumferentially a small amount and having its operative surface rounded-off somewhat.

In the depicted configuration the spiral arrangement has the dual functions of being the primary fastening means for the device to the fetus and being also the active electrode for, say, the monitoring of the fetal ECG. The spiral electrode 5 is attached (e.g. by soldering) to a lead wire 7. A reference electrode 8 for the ECG measurements is in the depicted example secured to the surface of the mid portion 2 of the base and is likewise connected to a lead wire 7. The plastic base 1 holds the electrodes in place and encapsulates the solder joints.

Via the bore 4 the base 1 also serves to provide a suitable mechanical mount for holding a probe, for example a pH electrode, reliably in position, during say the monitoring of the fetal tissue pH.

Figure 4:
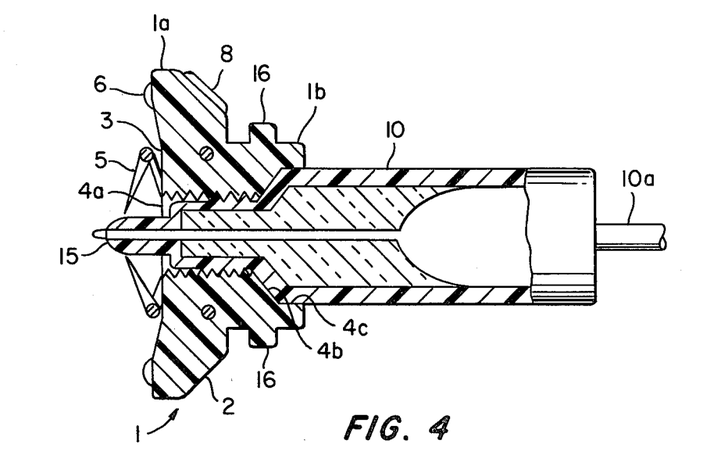
FIG. 4 is a partial sectional side view of the securing device of FIGS. 2A and 2B with accompanying probe, in accordance with the invention.

In practice, the operative surface of this relatively wide-based, double-helix screw electrode device is comprised of a cup-shaped flange having preferably a 1-cm diameter that conforms to the fetal scalp 9 and has as the bore 4 a central (axially running) threaded core for housing and securing the (pH, $pO_2$ or $PcO_2$) probe or electrode 10 (FIG. 4).

Figure 3A:
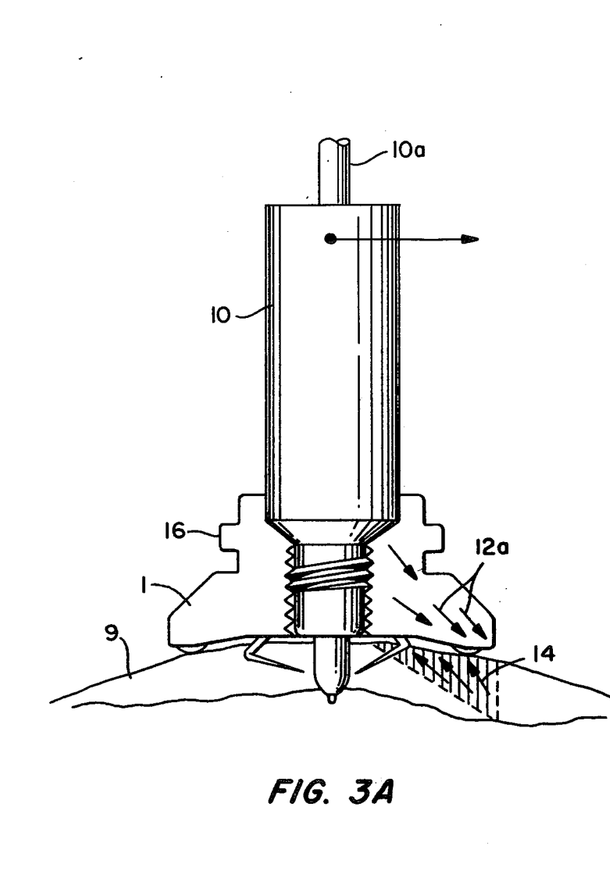
FIGS. 3A and 3B illustrate the manner in which the probe-securing device of FIGS. 2A and 2B safely distributes the forces encountered on and by the probe of the fetal scalp and the tissue volume therebeneath.
Figure 3B:
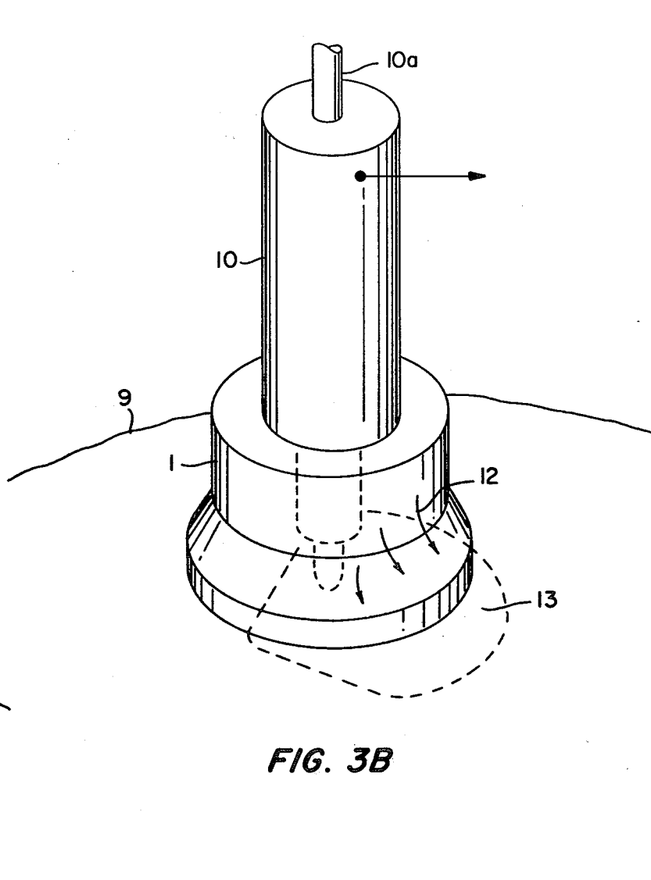

Referring to FIGS. 3A and 3B, the aforementioned embodiment of a fixation device for affixing a pH (tpH) probe to the fetal scalp during labor is illustrated in a way for demonstrating the device's capability of reducing and minimizing the adverse effects of the various force loads to be encountered in such circumstances. In contrast to the depicted prior art device of FIG. 1, in which substantially all forces are transmitted to the screws, as indicated by the arrows 11, the stresses of bending and shear in the device according to the invention (FIG. 3B) are spread through the volume of the fixation device, i.e. through the trangular cross-section buttresses, as indicated by the arrows 12, to the operative surface 3. From there these stresses are further distributed along the relatively large skin surface area and volume therebeneath, as indicated at 13 in FIG. 3B. This whole volume absorbs and resists the bending (rocking) and shear forces. In addition, these loads are also transmitted to the three pods. The pods 6 prove to be particularly advantageous, in terms of stability of the fixation device, if the skin is irregularly depressed at the monitoring site.

Figure 1:
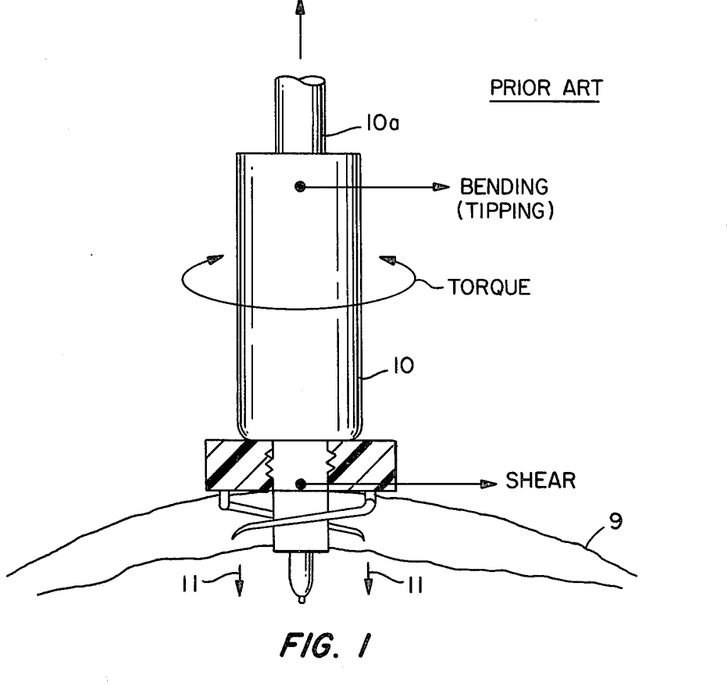
FIG. 1 is a prior art arrangement for securing probe to the fetal scalp, illustrating the various adverse forces which may be eoncountered thereby.

The relatively large area and volume 13 of intact tissue shown in FIGS. 3A and 3B amounts to a restoring stress distribution area which provides more total force resisting bending with substantially less stress concentration than prior art configurations such as shown in FIG. 1, and thus is able to fix the tpH probe 10 (FIG. 4) and help minimize the effects of bending (and/or shear) motion. FIG. 3A in particular illustrates by way of arrows 12a and 14 the countering resistive forces spread about the triangulated body of the fixation device and the time below.

The pods 6, located on the skin surface proximate the rim of the flange and the general friction of the relatively large surface contact area of operative concave surface 3, help provide stable support and prevent the device from being rotated by e.g. torque on the cable of the secured pH probe 10, by spreading the torque, and thus preventing unscrewing of the electrode or excessive screwing thereof into the skin. Since torque is generally recognized as the most detrimental effect of tension (pulling on the probe's cable), these measures will reduce the effect of tension. The stability provided by this design accordingly prevents tissue damage through reducing motion of the helical screw tips while providing a stable secure base for the pH electrode.

Further, this base design in being shaped to fit the curvature of the fetal skull, produces, along with the sealing effects of the fluids present during labor, a suction effect and good sealing of the wound (required to be made for say pH monitoring) from air and debris.

With the inclusion of a pH or some other kind of probe of similar size and shape, the bending loads or forces become the prime problem. Yet, the device according to the invention is able to provide distribution of the bending forces to a relatively large volume of tissue, and thereby produce only small local stresses, and thus minimize tissue defunction. The retaining screws 5 therefore experience minimal forces and displacement, thus reducing tissue stresses and damage.

FIG. 4 in particular shows the capability of providing the probe 10 in a perpendicular orientation relative to the operative surface 3 and therefore also to the presenting part of the fetus, as is considered required for best operation of the pH probe. Probe 10 has a threaded portion which screws into the threaded front portion 4a of the axial bore 4 and a rearward larger portion which seats into the larger portions 4b and 4c of the bore 4.

An important advantage of the arrangement depicted in FIG. 4 derives from the cup-shaped operative surface 3 which allows the spirals to draw the tissue into the recessed area and thus away from the scalp. This provices a safer base for the pH electrode 10. By deepening the recessed area even more than is actually shown, one could render the device safer yet, as the skin would tend to be drawn up further away from the scalp.

With the arrangement illustrated in FIG. 4, one is able to provide a fault indication if the pH electrode is not properly seated in the subcutaneous tissue (under the skin, immune from air or external body fluids as amniotic fluid). Improper seating results in false low pH readings which may not be distinguishable from true low readings. Improper seating can be detected as follows.

The pH electrode contains a reference electrode which is connected to body fluids by a low resistance "salt bridge" (KCl solution) 15. If the salt bridge 15 is in the subcutaneous space, and the wound is not open and gaping, one should measure a substantial resistance between the salt bridge and the skin surface (measurement #1). This could be accomplished via electrode 8 since during labor there are fluids present which would enable electrode 8 to be in contact with the fetal skin exterior. Alternatively, one could record the fetal ECG between the salt bridge and the usual EGG reference electrode 8 of the spiral electrode arrangement (measurement #2). In addition, there should be no ECG and essentially no resistance between the pH reference electrode and the spiral probes because they are both in the same low resistance subcutaneous fluid (measurement #3). Finally, to ensure that the spirals are properly placed, one should be able to record the fetal ECG between the spirals 5 and the reference electrode 8 (measurement #4).

The user in any event has the option of doing only some rather than all of the above four measurements. For example, one could perform measurements #2 and #4 without having to perform the others. Likewise for measurements #2 and #3.

Referring to FIGS. 5, 6A-6B and 7A-7B, 7B, a novel, disposable applicator tool arrangement has been devised for the application of a spiral electrode device and a pH electrode, such as are depicted in FIGS. 2-4, to the fetal scalp, and to make it possible to perform the procedure without an amnioscope and without visualization, i.e. by palpation without assistance. The applicator tool arrangement is comprised of a pair of concentric tubes, preferably made of plastic. The first is an inner tube 20 which holds the spiral electrode 1 and the other is an outer tube 30 for locking the inner tube 20 onto the spiral electrode 1. The spiral electrode is held by a pair of oppositely disposed tabs protruding transversely from the rear portion 1b of base 1 engaging with a pair of oppositely disposed cooperating slots 21 in the wall and proximate the one end 24 of inner tube 20. It will be apparent that the tabs could alternatively be provided on the inner surface of the inner tube 20 at the location of slots 21 and suitable cooperating recesses could be provided on the rear portion 1b of the base 1 in the location of tabs 16. Tube 20 is inserted into locking tube 30 so that its end 24 projects from the one end 32 of the locking tube to enable the spiral electrode 1 to be engaged with the tube end 24. Then, tube 20 is retracted into tube 30 by pulling on the hex-shaped flange 22 on the other end 25 of tube 20, thus then allowing the end 32 to surround the rear portion 1b of the spiral electrode and thereby locking the same into place on the inner tube 20.

Figure 5:
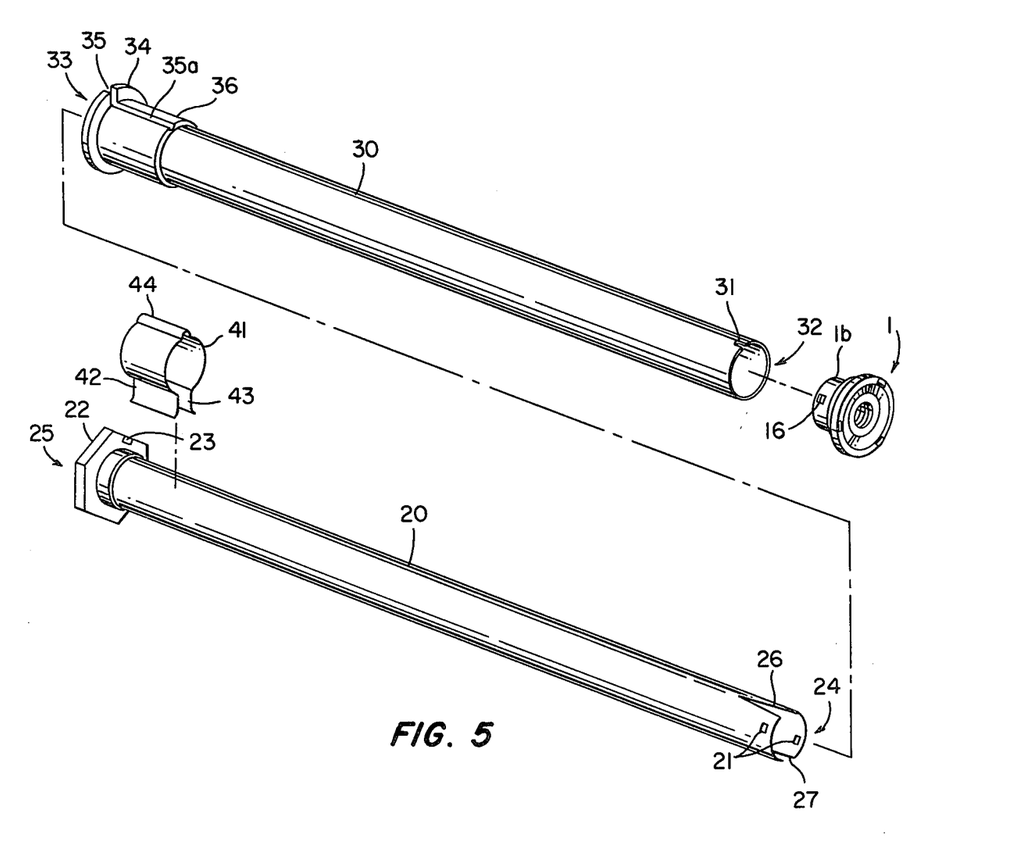
FIG. 5 illustrates in an exploded view an applicator tool assembly for effecting the attachment of the holder device of FIG. 2A to the fetal scalp.

The assembly of tubes 20 and 30 is used to apply the spiral electrode arrangement to the fetal scalp. The inner tube 20 may be rotated within locking tube 30 by way of the hex-shaped flange 22 provided at the opposite end 25 of tube 20. The torque thus created on the spirals 5 of the fastening device 1 causes the latter to be screwed into the fetal scalp.

Figure 6A:
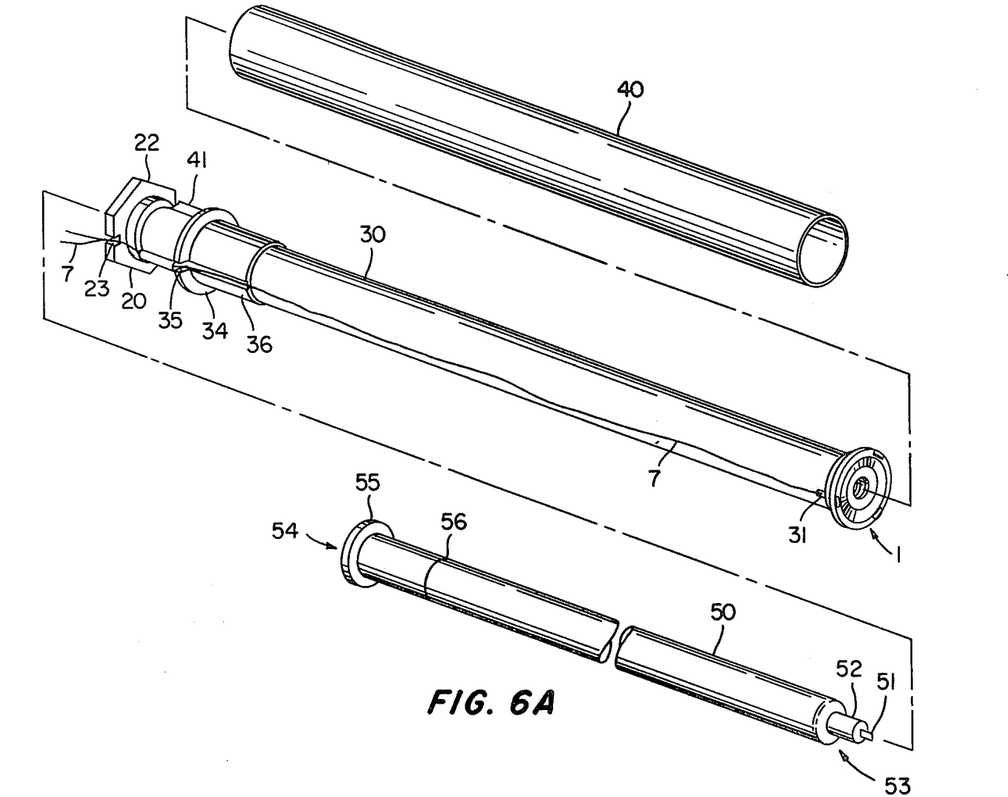
FIG. 6A illustrates in an exploded view an assembly of the parts illustrated in FIG. 5 in conjunction with a protective outer tube and a stab tool.

The hex-shaped plastic end 22 is shown as a separate piece in FIGS. 5-7. However, it will be appreciated that tube 20 may be constructed as a single piece. The flange portion of hex-shaped piece 22 has a slot 23 provided therein to conveniently receive the wires extending from the spiral electrode, as is particularly shown in FIG. 6A. A slot 31 is also provided at the one end 32 of locking tube 30 which provides a convenient egress for the wires 7. Locking tube 30, moreover, is provided at its other end 33 with an end piece 36 having an annular flange 34, which likewise has a slot 35 and associated groove 35a for the wires 7. Although end piece 36 is shown as a separate piece, locking tube 30 may be provided as a single (molded) plastic piece. It will be appreciated that tubes 20 and 30 are preferably made of plastic for the disposability aspect, but may be made of any other suitable material capable of performing the functions required thereof.

Torque tube 20 is also provided at end 24 with a pair of oppositely disposed wedge-shaped slits 26 which facilitate engagement and disengagement of the fixation device 1 from tube 20.

FIG. 6A illustrates the torque tube 20 and locking tube 30 in the assembled state with the spiral electrode 1 locked in place, ready for application to the fetal scalp. The position of locking tube 30 in place is ensured by placing a plastic, generally cylindrically shaped spacer clip 41 (FIGS. 5 and 6A) between the flanges 22 and 34 of the respective tubes 20 and 30. Spacer clip 41 has a pair of expanders 42 which run parallel to one another and along a longitudinal cut 43 in clip 41. Expanders 42 facilitate the attachment and removal of the clip 41 to respectively from the shaft of locking torque tube 20. As is particularly shown in FIG. 6A, spacer 41 has opposite the cut 43 a longitudinally running internal channel 44 for ensuring that the wires are retained in slots 23 and 35 and yet do not interfere with the manipulations for securing the fastening device to the fetus while spacer 41 is in place between flanges 22 and 33.

As is illustrated in the exploded view of FIG. 6A, the assembly comprising electrode 1, inner or torque tube 20 and locking tube 30 is inserted into an outer protective guide tube 40. The assembly is now ready for insertion into the vagina. It will be appreciated that outer tube 40 may completely house the spiral electrode device 1 within its interior, thus avoiding the possibility of the spirals snagging on the vagina walls during insertion. Notwithstanding, it will be appreciated particularly from FIGS. 7A and 7B that should the spiral fixation device 1 be allowed to protrude somewhat from the end of the outer tube 40, the relatively large diameter of the electrode's operative face 3 with respect to the diameter of the space between the spiral tips is more than sufficient to keep the vaginal walls away from the spiral ends and thereby avoid any snagging. As such, the plastic protective outer tube 40 is an optional element.

Figure 7A:
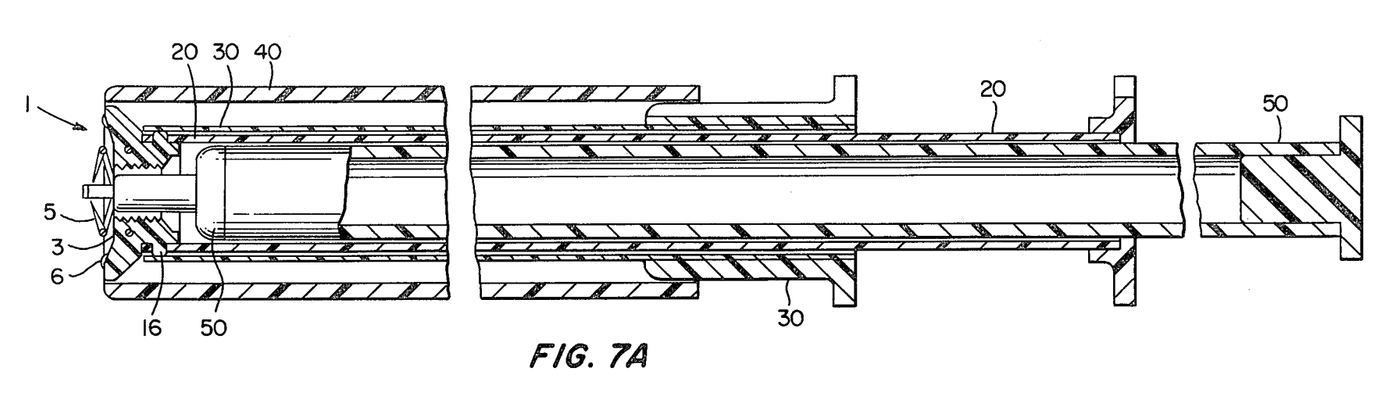
FIG. 7A is a cross-sectional side view of the complete assembly of FIG. 6A.

With the electrode attached to the fetal scalp (as is more particularly described hereinafter), the assembly is now ready for insertion of the stab tool or stylet 50. The stab tool 50 is a tubular device having at the one end 53 a tiny single knife blade 51 with the knive edge thereof oriented perpendicular to the tubular axis. The knife blade 51 extends from a short, small diameter rod 52 which in turn protrudes from the end 53 of the main tubular body of the stab tool 50. The stab tool is provided at its other end 54 with a flange 55 which facilitates, following insertion of the stab tool into the hollow of inner tube 20, the making of the stab wound in the fetal scalp and the subsequent removal of the stab tool from tube 20. Also provided on the outer surface of the main tubular body of stab tool 50 is a line 56 marking for the user the general point at which the stab blade 51 has in relation to the flange 22 of tube 20 reached a projection depth of 3 millimeters from the operative face 3 of the holder 1. FIG. 7A particularly illustrates the assembly of the outer tube 40, the locking tube 30, the torque tube 20 and the holding device 1 together with the tubular stab tool 50.

Figure 6B:
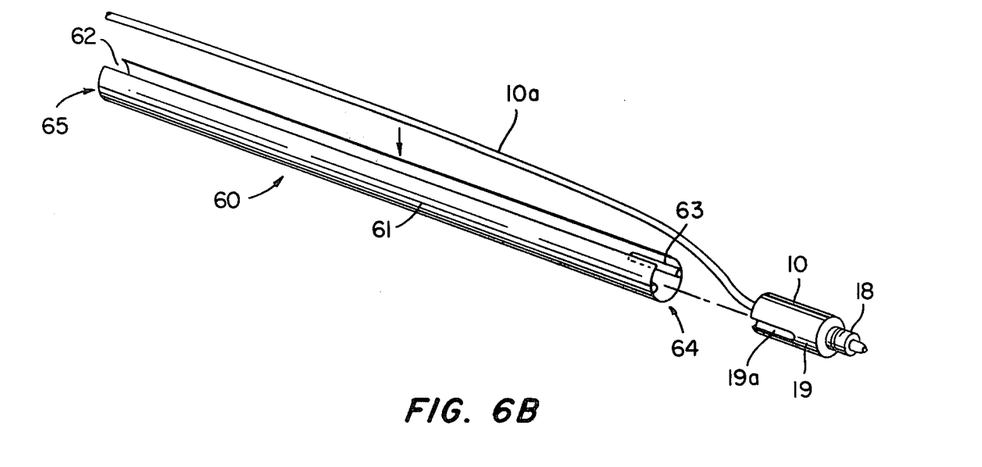
FIG. 6B illustrates the probe to be secured to the holder device of FIG. 2A together with the applicator tool for attaching the probe to the holding device.

After the stab wound has been made and the stab tool 50 withdrawn from the assembly, the latter is prepared for receiving the pH electrode itself. The pH electrode 10 is shown in FIG. 6B in an exploded or detached view with respect to its applicator tool 60. The applicator tool 60 is designed for inserting the pH electrode into the torque tube 20 from the flanged end 22 and urged along the length thereof until the threaded portion 18 of the operative end of the probe 10 meets the threaded bore 4 of the spiral holder 1. The probe's applicator tool 60 is comprised of an elongated tube 61, preferably disposable and made of plastic, and having a slot 62 in the side thereof which extends from one end 64 to the other 65. At the one end 64 a pair of elongated rounded ridges 63 are provided opposite one another inside the tube 61 which are intended to engage the body 19 of the pH probe 10 (FIG. 6B). In particular, a pair of longitudinally extending grooves 19a are provided in the surface of the electrode body 19 which extend from the rear end of the probe to approximately the mid section thereof. These grooves 19a are oppositely disposed on the probe 10 to align with the ridges 63 of the one end 64 of probe applicator tool 60. It will be appreciated that other suitable cooperating arrangements can be utilized, apart from the depicted interacting probe grooves 19a and applicator tool ridges 63, to enable the probe 10 to be demountably secured to the operative end 64 of tool 60.

Figure 7B:
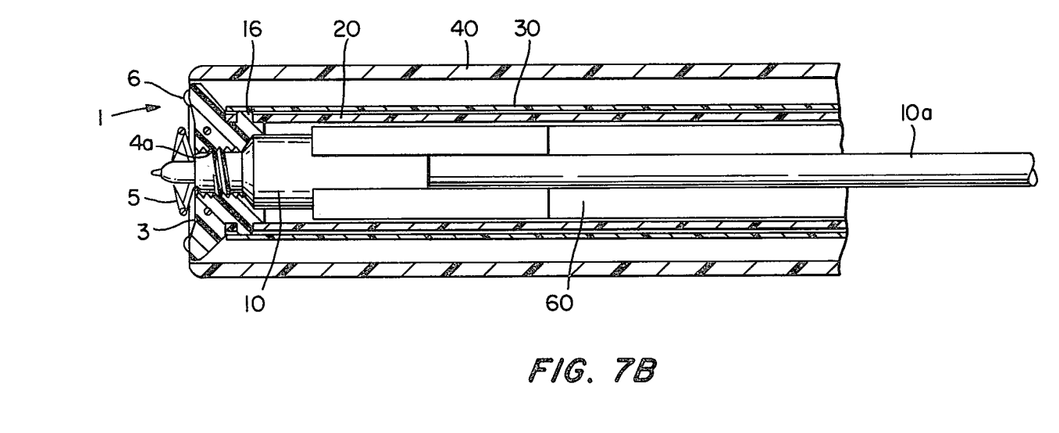
FIG. 7B is a cross-sectional side view of the assembly of FIG. 7A with, however, the stab tool replaced with the probe and its applicator tool.

FIG. 7B particularly illustrates the electrode 10 fully inserted into the applicator tool 60, and inserted into the hollow of torque tube 20 to be fully screwed into the threaded bore 4a, and thereby having the probe tip properly inserted into stab wound created by the stab tool 50. Longitudinal slot 62 (FIG. 6B) enables the cable 10a to be placed inside the applicator tool 60 when assembling the pH electrode 10 onto the end of the tool.

Figure 8A:
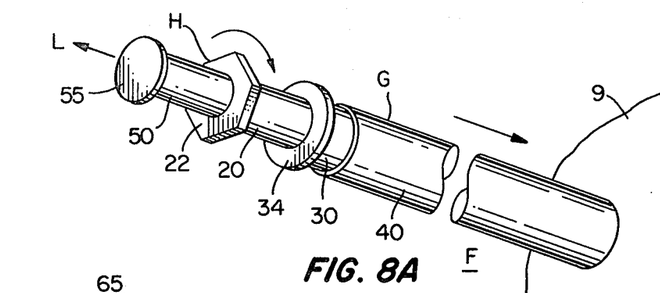
FIGS. 8A–8C illustrate the various manipulations required of the applicator assemblies illustrated in FIGS. 7A and 7B for attaching the holder device and probe of FIG. 4.

A main reason for the applicator tool assembly described above in connection with FIGS. 5-7 is to provide an easy method of attachment of the spiral device 1 and the guiding of the stab blade 50 and the pH electrode driver tube 60 to the center bore of the spiral device. The assembly is described below from an operative standpoint with reference to FIGS. 8A-8C.

The spiral device 1 is held in the jaws 27 of the plastic clamping device 20 (FIG. 5) which is locked onto the spiral device by the relatively rigid concentric outer locking tube 30 (FIGS. 6A and 7A). The locking tube 30 is held in place with the removable spacer 41. Projections on the rear portion 16 of the spiral fixation device 1 mate with holes 21 in the jaws of the clamping tube 20 to provide a positive lock for rotation and traction (FIG. 5). The outer protective tube 40 may be used to protect the spiral and clamping tube from contamination during insertion (FIGS. 7A-7B). The notches 31, 23 and 35 are for dressing in ECG wire 7 respectively in the jaws 27 of the clamp 20 and in the handles of both the locking tube 30 and the clamping or torque tube 20.

The stylet, having a $2 \times 2.8$ millimeter stab blade 51, is inserted through the center of the clamp tube 20 and spiral device 1. The flange or disc 55 on the end 54 of stab tool 50 allows pressure to be applied by the thumb to effect the stab wound.

The slotted pH driving tool 60 with its special ridges 63 for engaging the slots 19a on the pH electrode 10 provides a positive lock for rotation.

Before actual use, the sterile clamping tube 20, locking tube 30 and spiral device 1 are assembled, with the spacer then being placed as shown (FIG. 6A) to keep the spiral device 1 locked in the clamping tube 20 by preventing the locking tube 30 from sliding. The sterile stylet 50 is then placed inside. The pH probe driving tube 60 and pH electrode 10 should also be assembled at this point.

The clamping tube 20 and the outer tube 40 may be made of medical grade high density polyethylene.

In operation, one first slides the locking tube 30 onto the clamping tube 20, as indicated in the exploded view of FIG. 5, until the respective knobs or flanges 22 and 34 touch. The spiral fixation device 1 is then placed in between the jaws 27 of the clamping tube 20, with the wire 7 on the side of the notch 23 in the clamping tube's handle. The locking ears 16 of the spiral device 1 are placed into the small slots in the clamping tube between the jaws 27 and the locking tube 30 is then slid down onto the spiral device 1. The spacer is placed in FIG. 6A as shown, with the wire 7 being dressed through the various slots 23 and 35.

The stylet 50 is then placed into the clamping tube 20, and the blade 51 well into the center hole 4 of the spiral device 1, with the tip of the blade near the skin surface 9. This will place it in the correct position for later use.

Next, the pH electrode cable 10a is placed inside the drive tube 60 and the ridges 63 (FIG. guided 6B) into the slots 19a on the electrode 10.

If desired, the above assembly can be placed into the outer protective tube 40, leaving the spiral device 1 recessed about ½ inch (1 centimeter) therein.

The assembly may be inserted (F of FIG. 8A) and placed, (i.e. guided with the hand up the vagina, to a safe place on the fetal scalp) under direct vision through a 3 cm amioscope or a speculum. When used under direct vision, it is not necessary to use the outer protective tube 40.

Once applied to the desired place, the assembly is steadied by the hand (G of FIG. 8A) and the spiral device 1 is advanced to the fetal skin surface 9 and then, while a slight pushing pressure is maintained, the torque tube 20 is rotated about 180° clockwise (H of FIG. 8A) until the spiral "locks" (when resistance to turning is felt).

Figure 8B:
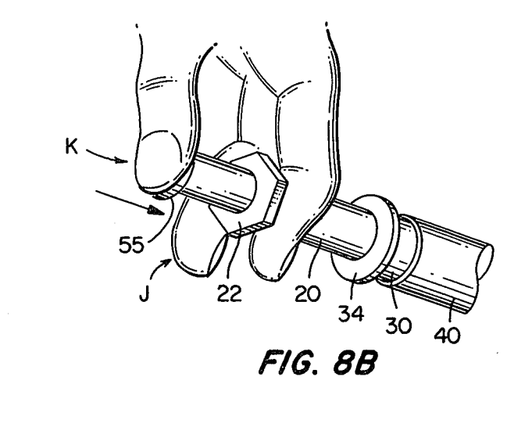

Using the hex knob 22 of the clamp 20, the scalp skin 9 is retracted by slowly and gently pulling on the knob 22 with the first and second fingers, as illustrated at J of FIG. 8B. While retracting, the incision may be made either with the other hand or the thumb, as illustrated at K in FIG. 8B. In FIG. 8B the incision is indicated as being made by pushing the stylet 50 with the thumb while retracting with the fingers. When the mark 56 lines up with the hex knob 22, there has been a 3-millimeter protrusion of the blade from the operative surface of the holder device 1.

The blade should be pressed decisively and firmly to produce a clean incision through the skin. The stylet 50 is then withdrawn (L of FIG. 8A).

While holding the hex knob 22 with one hand, with the other hand the assembled pH electrode-drive tool 10/60 is inserted through the clamping tube 20 into the center hole 4 of the spiral electrode device 1. The hex knob 22 is held to prevent the spiral device 1 from turning and the pH electrode 10 is screwed into the spiral device. Once the threads engage it will lock in about three turns (M in FIG. 8C).

Figure 8C:
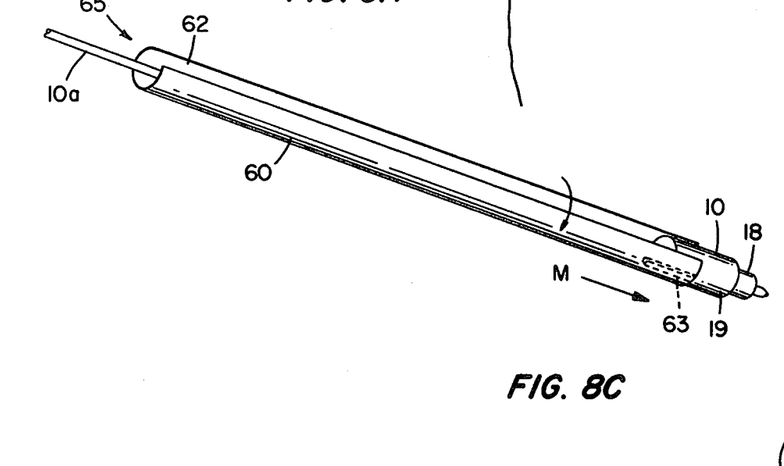

The driver tool 60 may then be used to try to turn the spiral device 1 a little further to make sure the assembly is well seated.

The cable 10a should be checked to see that it is not twisted and preferably is lying loose (i.e. disconnected from the electronics).

One now withdraws the driving tool 60, removes the spacer (N at FIG. 8C) and slides the locking tube 30 back along the clamping tube 20 (O at FIG. 8C) to release the spiral electrode 1. The clamp tube 20 and the locking tube 30 are then removed (P at FIG. 8C) by sliding them over the end of the cable 10a. The various connections to the electronics are then effected.

If the subcutaneous space has been entered, the pH will appear immediately. If the skin is not penetrated, the pH value will remain less than 7.0. If the electrode is marginally within the skin or subcutaneous space, a very erratic pH graph will likely be produced, and there will be sudden changes of >0.04 units with slight motion of the pH electrode 10, as by turning the cable 10a.

FIGS. 9A–9D illustrate a preferred interacting arrangement of the locking tube 30 and the clamping (torque) tube 20 for enabling a positive release of the spiral device 1 from the clamping tube. Instead of merely relying on the memory of the plastic material wherein the jaws 21 of the one end 24 of the clamping tube 20 are deliberately biased apart from one another in the material itself, release is assured by a cam arrangement. In the depicted embodiment of FIGS. 9A–9C, oppositely disposed disc-shaped cam surfaces 37 are provided on the inside wall of locking tube 30 proximate the one end 32 thereof. When clamp tube 20 is inserted into locking tube 30 the jaws 27 of the one end 24 thereof are oriented such that the cam surfaces 37 are located therebetween in the slots 26.

Figure 9A:
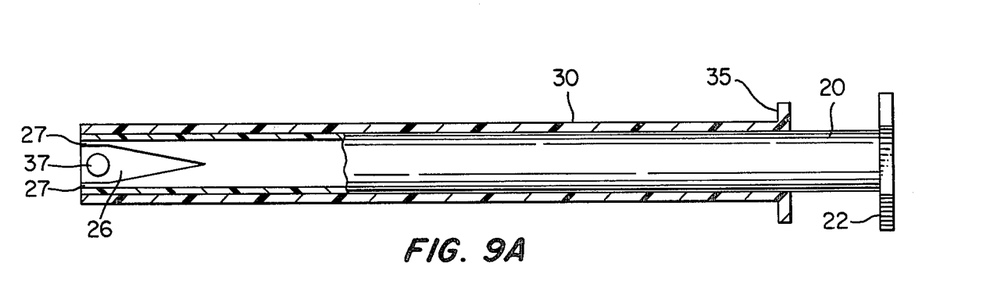
FIGS. 9A–9D illustrate in an end (9B) view and cross-sectional side (9A and 9C–D) views the clamping tool and locking tool assembly of the applicator assembly interacting via a dual cam arrangement for effecting positive release of the holder device of FIG. 2A from the applicator assembly.
Figures 9B, 9D, 10A, 10B:
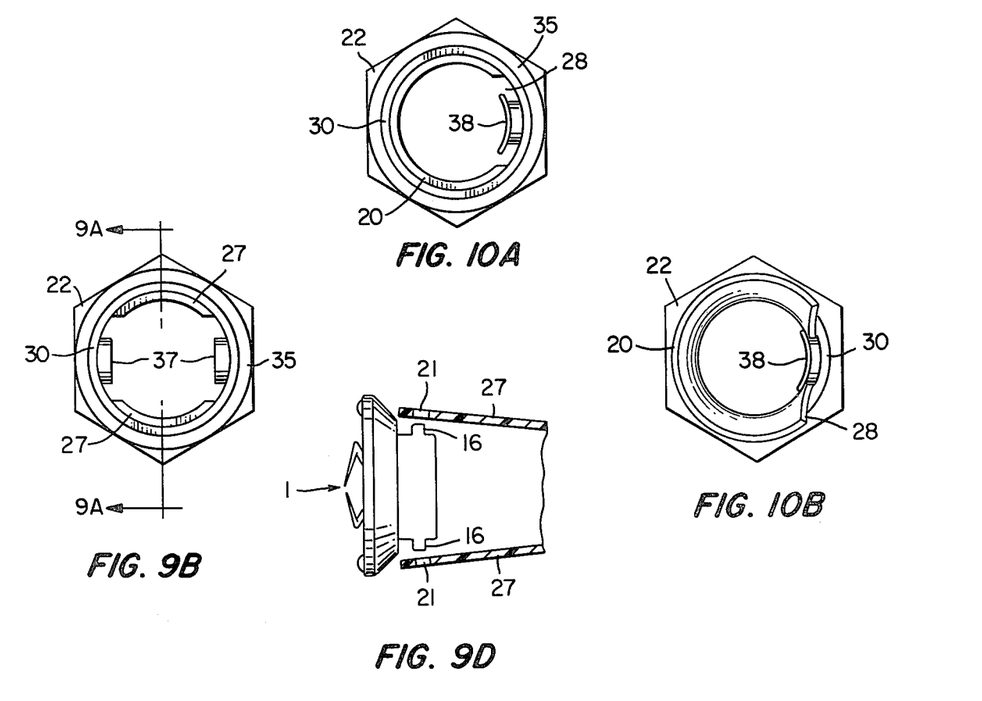
FIGS. 10A and 10B illustrate in end views the locked and released positions of the clamping tool and locking tool as the same positively interact via a single cam arrangement.
Figure 9C:
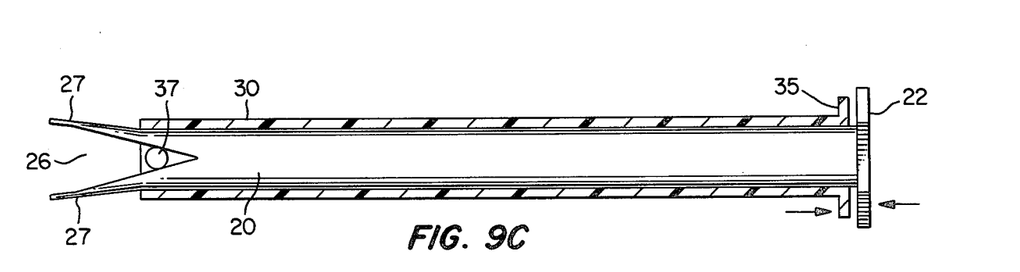

If the flange 35 of locking tube 30 and the flange 22 of the clamping tube 20 are urged toward each other, the result, as shown in FIG. 9C, will be the cam surfaces 37 advancing further into the slots 26 until the jaws 27 become positively separated from each other. A continuation of this advancement ultimately results in the cam surfaces 37 forcing the jaws apart sufficiently to permit a release of the spiral holder 1 from the slots 21 near the one end 24 of the clamping tube 20, as is shown in FIG. 9C.

An alternative preferred arrangement to that shown in FIGS. 9A–9C is a single-cam arrangement as depicted in FIGS. 10A–10B. Here, the end 24 of the clamping tube 20 may be provided with but a single slot 28 extending longitudinally along the shaft and shaped like the slots 26 shown in FIG. 9A. It will be appreciated that the dual slotted arrangement of tube 20 shown in FIG. 9A could also be used in connection with a single cam arrangement on the locking tube 30. FIGS. 10A and 10B illustrate respectively the locked and released positions, with FIG. 10B showing in particular that the opening of tube 20 is spread to a larger circumference by the positive action of the cam 38. The cam surface of cam 38 is more complex than those shown in the arrangement of FIGS. 9A–9C. And, it will be appreciated that the type of cam surface shown in FIGS. 10A and 10B could be employed in the dual-cam arrangement of FIGS. 9A–9C. The cam 38 of locking tube 30 in FIGS. 10A and 10B is a basically cylindrical protuberance, having a smaller diameter at and proximate the wall of the tube 30. The free end of the cam is provided with a larger diameter flange surface such that when the locking 30 and torque 20 tubes are arranged in the release position, the flange portion overlaps the edges of the cam slot 28. The wide end surface of the cam 38 is made concave. This factor together with the short length of the cam 38 ensure that the cam does not interfere with the passage of the stab tool end pH electrode through clamping tube 20.

Figure 11:
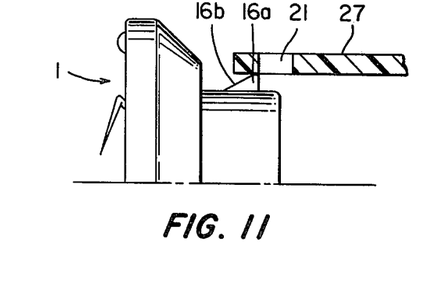
FIG. 11 illustrates in a partial side view a modification of the locking tabs of the holding device of FIG. 2A.

In order to further facilitate release of the spiral holder 1 from the clamping tube 20, the locking tabs on the rear portion 16 of the holder may, as shown in FIG. 11, have the forward transverse edge 16b angled substantially so as to eliminate the possibility of that edge hanging up on the adjacent edge of the slot 21 when attempting to withdraw the clamping tube 20 from the rear portion 1b of the spiral holder 1 and its tab 16a. A preferred angle for this forward edge 16b is 45°. This angled surface provides the additional beneficial effect of aiding in the cam action that spreads apart the opening of clamping tube 20.

In the attachment of devices to, or into, or particularly through the skin, it should be safer to hold the skin retracted from the underlying tissues to produce a real subcutaneous tissue space for the probe from the virtual space, and, in addition, to hold the probe away from the underlying tissues.

Referring to the arrangement of FIGS. 12A–12D there is depicted therein a fastening device which pulls skin into it to produce real space of the virtual subcutaneous space for placement of the pH electrode. This prevents the pH electrode from penetration past the subcutaneous space, yet allows penetration past the skin with safety.

In the embodiment of FIGS. 12A–12D, the cup-shaped device is attached to the skin as usual by threading the wire spirals into the skin. However, in the arrangement of FIGS. 12A–12D the spiral 5 is attached to a central hub 49 which, in turn, is threaded into the body of the fastening device 1 with a thread of the same direction as the spiral 5. Any suitable means may be employed to provide a certain resistance to the rotation of hub 49. By turning the device 1 into the skin with a clamping means on or around the device, and restraining the hub 49 from turning, such as via flat screw driving tool 58 (FIG. 12C), the spiral 5 can be fastened. By releasing the hub 49 thereafter and continuing to turn in the same direction, by way of clamping or torque tube 20, the threaded hub 49 would draw the spiral 5 and skin 9 into the recessed surface 3 of the device. A lock may be employed to fasten the hub 49 in place.

Figure 12A:
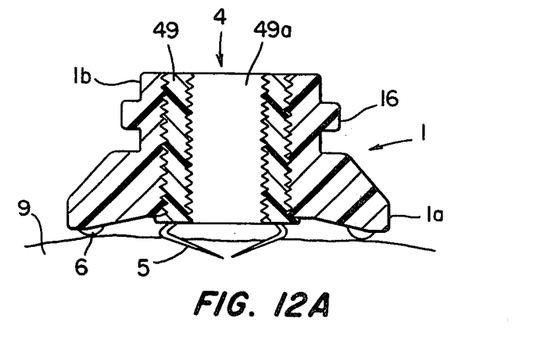
FIGS. 12A–12D are cross-sectional side views of the holder device of FIG. 2A, modified to include a threaded core piece for permitting selective variations of the depth of the probe into the fetal scalp.
Figure 12B:
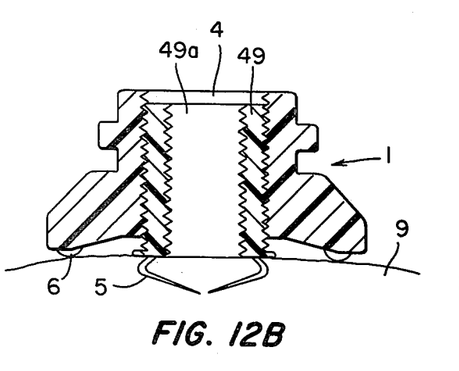

Referring to FIG. 12B, the initial or starting position may have the hub 49 partially emerging from the operative face 3 or the fastening device 1 to place the spirals 5 in closer approximation to the skin or to allow use of spirals which do not have to penetrate as far, and are thus less traumatic.

Figure 12C:
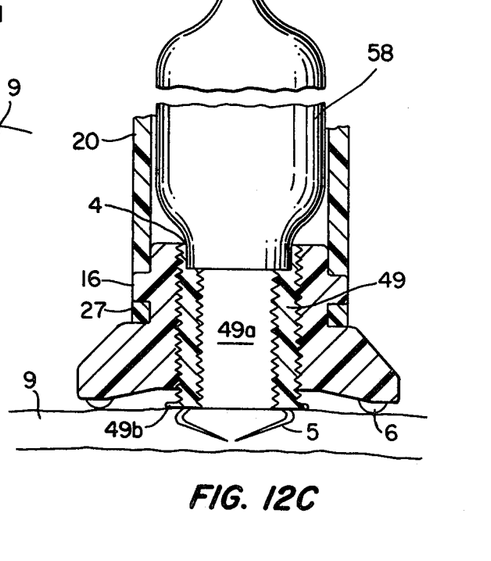

Referring to FIG. 12C, the fastening device 1 is held by the clamping tube 20. The bladed stop as driver tool 58 fits into a transverse slot (not particularly shown) in the top surface of the hub 49 and is used to prevent retraction of the hub while fastening the spiral 5 into the skin 9. The bladed stop 58 is then removed and the fastening device 1 is turned in the same direction by the clamping or torque tube 20, thus keeping the spiral 5 fastened into the skin. The threads between the hub 49 and the fastening device 1 cause the hub to retract into the cup-shaped surface 3, pulling the skin 9 with it via the spiral 5 until a limit stop 49b, in the form of an annular flange, prevents further retraction.

Figure 12D:
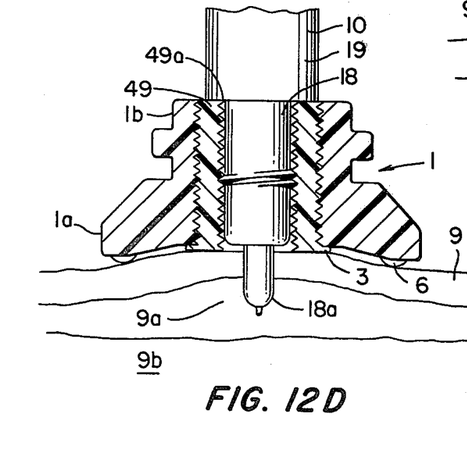

Referring to FIG. 12D, an incision may then be made through the skin 9 into the subcutaneous tissue pocket 9a with safety, and the pH electrode 10 threaded into bore 49a of the hub 49 while holding the fastening device 1 with clamping tube 20, again using a thread of the same sense as the spiral 5. This arrangement also may allow the cup-shaped device 1 and the hub 49 to pull the skin 9 up around the pH electrode 10. This may be accomplished by threading the spiral 5 into the skin 9 with the stop 58 in place, removing the stop, making the incision, and threading the pH electrode 10 partially through the hub 49. By then holding the pH electrode still and turning the cup-shaped device 1 with the clamping tube 20, the skin will be drawn up over the probe 10, the hub will stop and the probe will then penetrate until it stops. Multiturn fine threads and tight threads may prevent unscrewing of the hub 49 although low tissue tension will probably place little torque on this.

In another configuration, the hub 49 threads could be in a direction opposite the spiral. After fastening the spiral 5, the incision is made, the clamping tube 20 is used to hold the device 1, and the pH electrode 10 is rotated through a center thread in the same direction as the spiral 5. By continuing to turn the pH probe 10, the hub 49 will be drawn up, drawing the skin 9 and electrode tip 18a away from underlying tissue 9b.

Figures 13A, 13B, 14A, 15:
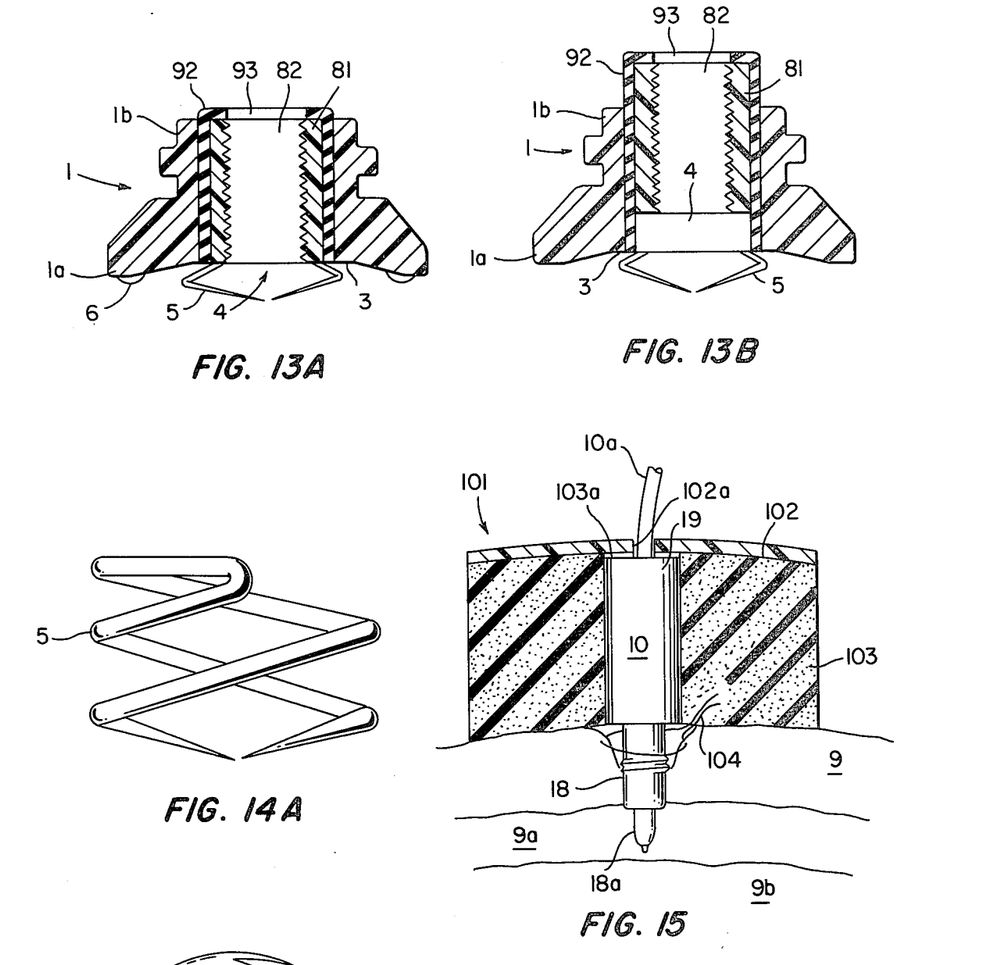
FIGS. 13A and 13B illustrate another modification of the holder of FIG. 2A wherein the central threaded hub is elastically secured to the remainder of the holder for providing automatic repositioning of the probe in response to the force exerted on the tip thereof.
FIGS. 14A and 14B illustrate in enlarged views the single wire helical arrangement by which the holder device of FIG. 2A is screwed to the fetal scalp.
FIG. 15 illustrates an alternative embodiment of a probe-holding device having particular use in non-fetal applications.

In addition to the advantage of being able to positively control the depth of the probe, as was described above, and to be able to retract the skin from the underlying tissue a few millimeters, there is also the desire to be able to automatically accommodate changes in pressure against the probe, especially if the skin becomes thinner and the probe should thus be too deep. In accordance with the invention, the basic fastening device 1 is modified as illustrated in FIGS. 13A and 13B to have a movable rigid inner piece or hub 81 containing the threads and bore 82 for accommodating the pH electrode 10. An elastic member 92 having a circular centered hole 93 is permanently fastened (e.g. glued) to the inner surface of the outer rigid portion (1a and 1b) of device 1, and to the top (distal) portion of the inner member 81. Any excessive force applied to the inner member 81 by way of the pH probe 10 would push against the elastic piece 92 and allow the electrode to move outward. Since the force would be proportional to displacement, small displacements would be accommodated, but the inner piece 81 would not be forced far enough for the probe to be out of the skin.

Figure 14B:
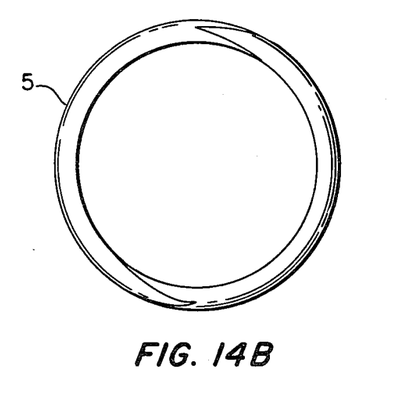

FIGS. 14A and 14B illustrate enlarged views of the single-wire spiral arrangement 5 which is partially embedded in the body of the fastening device 1 of, for example, FIG. 2A. The advantages of this particular spiral design are that the configuration allows economical manufacture of devices which require the spiral wire holding means and yet have a clear passage way (hole) through their center. This design permits a straight length of wire (e.g. stainless steel) to be ground to a needle point at both ends in the straight configuration. The wire can then be formed to a U-like shape and ultimately to the helical configuration shown. One very important additional advantage of this design is that the spiral wire breaks the surface of the fastening device 1 in such a way as to avoid any high stress point or fulcrum point on the wire itself, thus reducing greatly the chances of one of the exposed spirals 5 breaking off accidentally.

The pH electrode 10 depicted herein is designed for vertical insertion through the skin to the subcutaneous tissue. This may not be adequate or practical for monitoring in non-fetal situations (i.e. neo-nate to adult) because of the large number of sutures needed to hold the electrode perpendicular to the skin, the requirement that there be no motion of the site, and the chance of infection through the open wound.

There is proposed in connection with FIG. 15 a disposable pH electrode holder 101 for non-fetal use.

PH electrode holder 101 is comprised of a disc-shaped hard-plastic cap 102 and a relatively thick cylindrically shaped foam pad 103 which has an adhesive operative surface to secure it to the cap 102. The cap 102 has a radial slot 102a in it to allow the cable 10a and the pH electrode 10 to be inserted and held within the holder 101. The foam pad 103 is provided with a central hole 103a for snuggly housing the body 19 of the pH electrode 10. On the operative surface (away from the cap 102) of the cylindrical foam pad 103 the adhesive layer is provided with a peel-off paper cover (not particularly shown). The holder device may be utilized in accordance with the following.

After appropriate anesthesia and skin preparation a (3 mm wide) stab incision is made through the skin into the subcutaneous space or through the fascia. Under direct vision, the wound is spread with mosquito forceps to make sure it penetrates sufficiently. A purse string suture 104 is placed around the wound. The electrode wire 10a is slipped through the slot 102a in the electrode holder 101, with the holder distal to the pH electrode body 19. The pH electrode 10 is placed firmly in the stab wound. The wound may be closed tightly around the electrode with the purse string suture 104. The adhesive cover to the foam pad 103 is removed and the electrode holder 101 is slipped along the wire 10a until it is firmly attached to the skin 9. Since the hole in the retainer cap 102 is only large enough to admit the cable 10a, it places pressure on the hub or body 19. The foam pad 103 is slightly shorter than the hub 19, so the foam 103 is under tension, pushing gently on the electrode 10 with the cap 102. The hole 103a to hold the electrode 10 is slightly smaller than the hub 19 to provide a firm grip. In addition to holding the electrode in place, this arrangement maintains sterility by covering the wound.

To remove the electrode, the foam pad 103 is peeled off the skin 9 and slipped back on the wire 10a. The purse string suture 104 is cut and removed. The electrode 10 is removed, the wound cleansed and closed.

Figure 16:
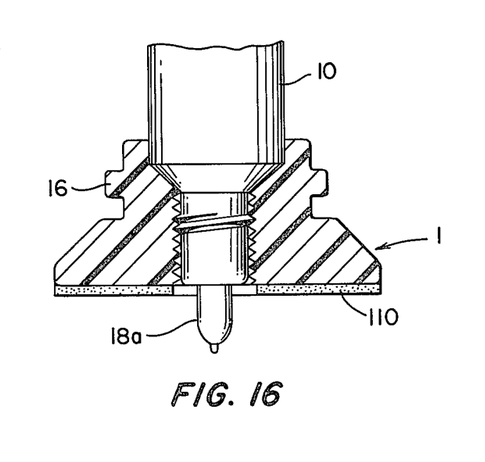
FIG. 16 illustrates another embodiment of a probe-holding device according to the invention also having particular use in non-fetal applications.

FIG. 16 illustrates an atternative arrangement for non-fetal use, in which effectively the entirety of the holder means 1 on the operative face side has been substituted by a flat surface on which is deposited a circular double-sided adhesive layer 110 having a central hole to pass the electrode tip 18a. The adhesive layer together with the broad operative surface provide the necessary attachment and stability for proper positioning and retention of the probe substantially perpendicular to the skin.

What is claimed is:

1. A device for detachably securing a bio-medical monitoring means which means comprises an elongated probe, into or through the surface tissue of an organ of an organism, such as the skin, the device comprising a surface base for attachment to the organ, having substantially cylindrically shaped rear and front body portions, with the latter having an operative end from which the operative part of the probe protrudes when in place, said operative end having a front surface, the area of which is substantially greater than the cross-sectional area of the protruding operative part of the probe, said front surface having means shaped for application to organ surfaces which are irregular, curved or deformable and for enabling the organs's surface tissue to be drawn away from the body of the organ when said base is being attached to the organ, said base defining a substantially centrally located passageway through said rear and front body portions and a corresponding aperture in said front surface for receiving the probe, at least the operative end of said front portion of the base having means for minimizing movement of the operative part of the probe due to tilting, torquing or other forces experienced by the probe remotely from the operative part thereof and for distributing such forces over a surface area of the organ which extends beyond the organ surface underlying said front surface, said base having means for securing the probe fixedly yet detachably in or through the surface tissue of the organ, said securing means including first means mounted on said operative end of said front portion for rotatably attaching the base to the organ surface and second means associated to said passageway for cooperative engagement with the probe, said first and second means providing direct access through said base to the surface of the organ underlying said front surface.

2. Apparatus according to claim 1 wherein said front surface includes third means for enhancing the distribution of said forces in the presence of an irregular, curved or deformable organ surface.

3. Apparatus according to claim 2 wherein said third means comprises at least three pods arranged proximate the periphery of said front surface equispaced apart from one another.

4. Apparatus according to claim 1 wherein said front surface is concave.

5. Apparatus according to claim 1 wherein said base includes means for guiding the monitoring means to the organ.

6. Apparatus according to claim 5 wherein said second means orients said probe substantially perpendicular to said front surface and therefore the surface of the organ.

7. Apparatus according to claim 1 wherein said first means is comprised of a single piece of wire having the ends thereof sharpened and which is configured to form a helical screw, with that portion of the screw which includes the wire ends partially protruding from said front surface.

8. Apparatus according to claim 1 wherein said first means comprises a helical screw made of conductive material and said monitoring means includes means connected to said screw for electrocardiographic monitoring of the organism.

9. Apparatus according to claim 8 wherein said electrocardiographic monitoring means includes a reference electrode mounted on the base.

10. Apparatus according to claim 8 wherein said monitoring means includes means assembled on the base for simultaneously monitoring both pH and ECG.

11. Apparatus according to claim 1 wherein said second means comprises an axial threaded bore through the base, and wherein said elongated probe has on a predetermined protion of its exterior a threaded portion for engaging said second means.

12. Apparatus according to claim 11 further including rigid member means positioned in said axial bore for adjustable engagement with said front and rear body portions of the base and wherein said first means is fixedly attached to said rigid member means.

13. Apparatus according to claim 12 wherein said rigid member means and said front and rear body portions are threaded for effecting said adjustable engagement.

14. Apparatus according to claim 13 wherein said first means is comprised of screw means.

15. Apparatus according to claim 14 wherein the thread engagement between said rigid member means and said body portions is of the same sense as said screw means.

16. Apparatus according to claim 12 further including an elastic connecting coupling said rigid member means to said body portions.

* * * * *